(12) United States Patent
Ishikawa (10) Patent No.: US 8,761,863 B2
(45) Date of Patent: Jun. 24, 2014

(54) TARGET TRACKING DEVICE AND RADIATION THERAPY APPARATUS

(75) Inventor: Masayori Ishikawa, Sapporo (JP)

(73) Assignee: National University Corporation Hokkaido University (JP)

( * ) Notice: Subject to any disclaimer, the term of this patent is extended or adjusted under 35 U.S.C. 154(b) by 218 days.

(21) Appl. No.: 13/203,565

(22) PCT Filed: Feb. 8, 2010

(86) PCT No.: PCT/JP2010/052133
§ 371 (c)(1),
(2), (4) Date: Sep. 9, 2011

(87) PCT Pub. No.: WO2010/098214
PCT Pub. Date: Sep. 2, 2010

(65) Prior Publication Data
US 2012/0041250 A1   Feb. 16, 2012

(30) Foreign Application Priority Data
Feb. 26, 2009   (JP) ................................. 2009-044881

(51) Int. Cl.
*A61B 5/05*   (2006.01)
*A61N 5/00*   (2006.01)
*G06K 9/00*   (2006.01)

(52) U.S. Cl.
USPC ............................... 600/427; 600/1; 382/131

(58) Field of Classification Search
USPC .............. 600/1, 424; 382/103, 132, 154, 128, 382/131; 378/65
See application file for complete search history.

(56) References Cited

U.S. PATENT DOCUMENTS

| 6,144,875 A | 11/2000 | Schweikard et al. |
| 6,307,914 B1 | 10/2001 | Kunieda et al. |
| 6,778,850 B1 | 8/2004 | Adler et al. |
| 2006/0074292 A1 | 4/2006 | Thomson et al. |
| 2010/0119037 A1 | 5/2010 | Kato et al. |

FOREIGN PATENT DOCUMENTS

| JP | 3-53389 B1 | 6/2000 |
| JP | 2003-202382 A | 7/2003 |
| JP | 2004-166975 A | 6/2004 |

(Continued)

OTHER PUBLICATIONS

Nittoh, K., Konagai, C., Noji, T., Development of multi-color scintillator based X-ray image intensifier. Nuclear Instruments and Methods in Physics Research A 535 (2004) 686-691.*

(Continued)

*Primary Examiner* — Jacqueline Cheng
*Assistant Examiner* — Kaylee Wilson
(74) *Attorney, Agent, or Firm* — Cantor Colburn LLP (57) ABSTRACT

A target tracking device for tracking a moving target, based on X-ray fluoroscopic images from a plurality of directions, the target tracking device may include a plurality of X-ray fluoroscopic devices, an image processing unit, and a position determining unit. The X-ray fluoroscopic devices obtain a plurality of images from a plurality of directions, each of the images in a given direction having a different sensitivity. The image processing unit identifies a position of a target image based on pattern matching between the plurality of images and an image of the target. The position determining unit determines a 3D position of the target based on the position of the target image in the plurality of images from the plurality of directions.

8 Claims, 7 Drawing Sheets

(56) References Cited

FOREIGN PATENT DOCUMENTS

| | | |
|---|---|---|
| JP | 2006-230673 A | 9/2006 |
| JP | 2008-23347 A | 2/2008 |
| JP | 2008-514352 A | 5/2008 |
| JP | 2008-251211 A | 10/2008 |
| WO | 00/54689 A1 | 9/2000 |
| WO | 2006/039009 A2 | 4/2006 |
| WO | 2008/132845 A1 | 11/2008 |

OTHER PUBLICATIONS

Extended European Search Report for Application No./Patent No. 10746095.8-2305/2401964, dated Jun. 25, 2012.

International Search Report for International Application No. PCT/JP2010/052133 mailed Mar. 9, 2010 with English translation.

Nittoh et al., "X-Ray Inspection System Using Color Image Intensifier", Toshiba Review vol. 59, No. 10 (2004), p. 51-54.

Notice of Grounds for Rejection for Japanese Patent Application No. 2011-501551, mailed Apr. 15, 2014. English translation attached.

\* cited by examiner

TARGET TRACKING DEVICE AND RADIATION THERAPY APPARATUS

This is a U.S. national stage application of International Application No. PCT/JP2010/052133, filed on Feb. 8, 2010. Priority under 35 U.S.C. 119(a) and 35 U.S.C. 365(b) is claimed from Japanese Application No. 2009-044881, filed Feb. 26, 2009, the disclosure of which is also incorporated herein by reference.

TECHNICAL FIELD

The present invention relates to a target tracking device for tracking a moving target, based on X-ray fluoroscopic images from a plurality of directions, and a radiation therapy apparatus utilizing the same.

BACKGROUND ART

In radiation therapy, accurate irradiation of the affected region (e.g., a tumor) is important. Meanwhile, a living organ moves in various manners, and a tumor positioned near a lung, in particular, moves largely based on respiration. Therefore, it has been proposed, with a marker placed near a tumor, to determine the position of the marker, using a bi-directional X-ray fluoroscopic moving object tracking device to control irradiation of therapy radiation (Patent Document 1). This moving object tracking device captures an image of a metallic marker or the like embedded in a body, using two sets of high-power X-ray producing device and X-ray image receiving devices, and measures the 3D position, based on two 2D fluoroscopic images. Successive capturing of X-ray fluoroscopic images enables real-time calculation of the 3D position of a metallic marker, and therefore, a metallic marker in a position subjected to respiration-caused movement can be detected with high accuracy. In view of the above, it is possible to irradiate radiation with high accuracy according to the movement of a tumor by controlling irradiation of therapy radiation, based on a result of detection of a metallic marker.

RELATED ART DOCUMENT

Patent Document

Patent Document 1: JP 3053389 B
Patent Document 2: JP 2006-230673 A
Patent Document 3: JP 2003-202382 A

Non-Patent Document

Non-Patent Document 1: Toshiba Review Vol. 59 No. 10 (2004) p. 51-54

DISCLOSURE OF THE INVENTION

Problem to be Solved by the Invention

Effective therapy radiation requires accurate determination of the marker position. In particular, when a low density region, such as lung, and a high density region such as bone coexist, tracking the metallic marker may be difficult.

Further, there has been a proposal related to X-ray irradiation by a moving object tracking device (see Patent Document 2), with further efficiency required. Note that expansion of a dynamic range of a radiation image by utilizing a color scintillator is described in Patent Document 3 and Non-Patent Document 1.

Means for Solving the Problems

The present invention relates to a target tracking device for tracking a moving target, based on X-ray fluoroscopic images from a plurality of directions, comprising an image obtaining unit for obtaining a plurality of X-ray fluoroscopic images having different sensitivities in one direction; a target determining unit for identifying a target in each of the X-ray fluoroscopic images in one direction through pattern matching, then, while employing a target with higher accuracy among targets at substantially identical positions in a result of identification, determining a position of the target in the X-ray fluoroscopic image in one direction, and carrying out the identification and the determination for the respective X-ray fluoroscopic images from the plurality of directions, to thereby determine a position of the target in the X-ray fluoroscopic images from the plurality of directions; and a 3D position determining unit for determining a 3D position of the target, based on the position of the target in the X-ray fluoroscopic images from the plurality of directions, determined by the target determining unit, wherein the 3D position determination for the target is repeated to thereby track the target.

Further, preferably, the image obtaining unit may obtain X-ray fluoroscopic images in a plurality of fluorescent colors according to the intensity of fluoroscopic X-rays.

Further, the present invention relates to a radiation therapy apparatus including the above described target tracking device, wherein irradiation of a radiation therapy beam toward a living organ is controlled based on the 3D position of the target.

Further, preferably, the target may be a marker embedded in the living organ.

Further, preferably, the marker may be made of material having a large electron density or a large X-ray stopping power.

Further, preferably, the marker may include two or more marker items.

Further, preferably, the target may be a tumor or a vertebral column in the living organ.

Further, preferably, the irradiation of a radiation therapy beam toward the living organ may be permitted or restricted only when the 3D position of the target is within a predetermined area.

Advantages of the Invention

According to the present invention, it is possible to obtain X-ray fluoroscopic images having a plurality of sensitivities in one direction, and to accurately detect a target, based on the images.

BEST MODE FOR CARRYING OUT THE INVENTION

In the following, an embodiment of the present invention will be described based on the following drawings.

Figure 1:
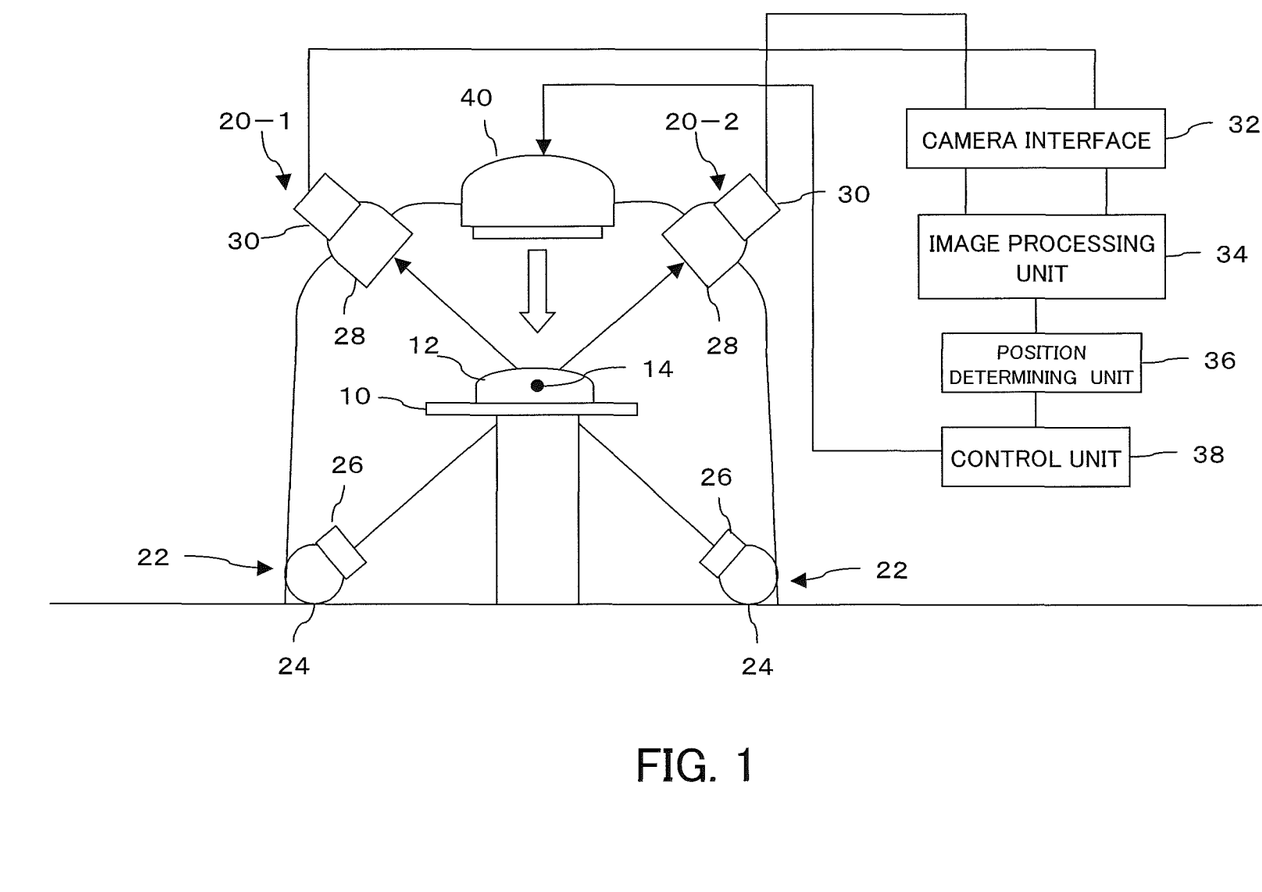
FIG. 1 is a schematic diagram showing a structure of a radiation therapy apparatus according to an embodiment.

FIG. 1 is a diagram showing a complete structure of a radiation therapy apparatus including a position determination device according to the embodiment.

A marker 14 is embedded in a patient 12 lying fixed on a therapy bed 10. The marker 14 is, e.g., a metallic ball having a diameter of 1 to 2 mm and embedded beforehand near the affected region. The marker 14 is embedded in a predetermined position near an affected part in the body, using a predetermined embedding tool. The marker 14 embedded as described above retains a constant positional relationship with the tumor, thus functioning as a relative positional marker of the tumor. Note that for the marker 14, a high electronic density material having large X-ray absorption is desirable, and specifically, oxide, ceramic, contrast medium, or metal having a large relative density, such as, gold, tungsten, and the like, is used.

Two X-ray fluoroscopic devices 20-1, 20-2 are installed near the therapy bed 10. The respective two X-ray fluoroscopic devices 20-1, 20-2 irradiate an X-ray to the patient 12 on the therapy bed 10 from different directions to separately obtain fluoroscopic images. The two X-ray fluoroscopic devices 20 have a basically identical structure with difference only in the direction of the X-ray beam. Therefore, the following description is common to both.

The X-ray irradiating device 22 comprises an X-ray tube 24 and a collimator 26, and irradiates a predetermined X-ray beam. An X-ray beam from the X-ray irradiating device 22 penetrates a predetermined part of the patient 12 on the therapy bed 10, and enters an opposed image intensifier 28. Then, the image intensifier 28 converts the incoming X-ray into light on an incident fluorescent surface, and discharges photoelectrons via the photoelectric film of the fluorescent surface. Then, the photoelectrons are accelerated by an electronic lens and converged onto an output fluorescent surface, where the photoelectrons are converted into a visible image. The visible image is then converted into an electric signal via a camera (e.g., a CCD camera) 30. The camera therefore outputs an image signal according to the incident X-ray.

Note that in the image intensifier 28, the output fluorescent surface is a multiple-color scintillator, and the camera 30 is a color camera. With the above, the incoming X-ray is converted into R, G, B signals having different sensitivities according to the intensity of the X-ray, and the camera 30 outputs RGB color image signals.

The image signals from the cameras 30 of the two X-ray fluoroscopic devices 20-1, 20-2 are input via the camera interface 32 into the image processing unit 34.

The image processing unit 34 carries out image processing with respect to the respective R, G, and B signal images from the two X-ray fluoroscopic devices 20-1, 20-2. In this embodiment, the image processing unit 34 processes an image received to identify a marker 14 embedded in the body of the patient 12. Then, data on the 2D coordinates of the marker 14 in the respective images obtained by the two X-ray fluoroscopic devices 20-1, 20-2 are supplied to the position determining unit 36. The position determining unit calculates the 3D position of the marker 14, based on the pre-known 3D coordinates of the X-ray irradiating devices 22 of the two X-ray fluoroscopic devices 20-1, 20-2 and of the image intensifier 28 and the coordinates of the marker 14 in the two images obtained, and supplies the 3D position calculated to the control unit 38. The control unit 38 controls a beam irradiation device 40, such as a linac, that irradiates a therapy radiation beam to the patient 12. That is, the direction of the therapy radiation beam from the beam irradiation device 40 is determined beforehand, and the position of the tumor to be irradiated is known based on the position of the marker 14. Therefore, the control unit 38 determines whether or not the tumor is within the irradiation range of the therapy radiation beam, and controls the beam irradiation device 40 so as to irradiate a therapy radiation beam only when the tumor is within the irradiation range. Note that the beam irradiation device 40 may irradiate a therapy radiation beam in a constant direction, or may irradiate while rotating. With the beam irradiation device 40 irradiating a therapy radiation beam while rotating, rotating intensity-modulated radiation therapy and so forth can be achieved.

In this manner, according to this embodiment, the position of the marker 14 is determined based on an image obtained on a real time basis by the X-ray fluoroscopic devices 20-1, 20-2, and irradiation of a therapy radiation beam from the beam irradiation device 40 is controlled. With the above, it is possible to reliably irradiate therapy radiation to a largely moving tumor, while following the tumor, so that unnecessary radiation irradiation can be avoided.

Note that although therapy radiation is irradiated only when the marker 14 is within a predetermined range in the above described example, the irradiation position of therapy radiation may be controlled while following the determined position of the marker 14. In the above, it is preferable to simultaneously recognize a sensitive organ, such as a spinal cord or the like, so that irradiation with the therapy X-ray beam thereto is avoided.

Figure 2:
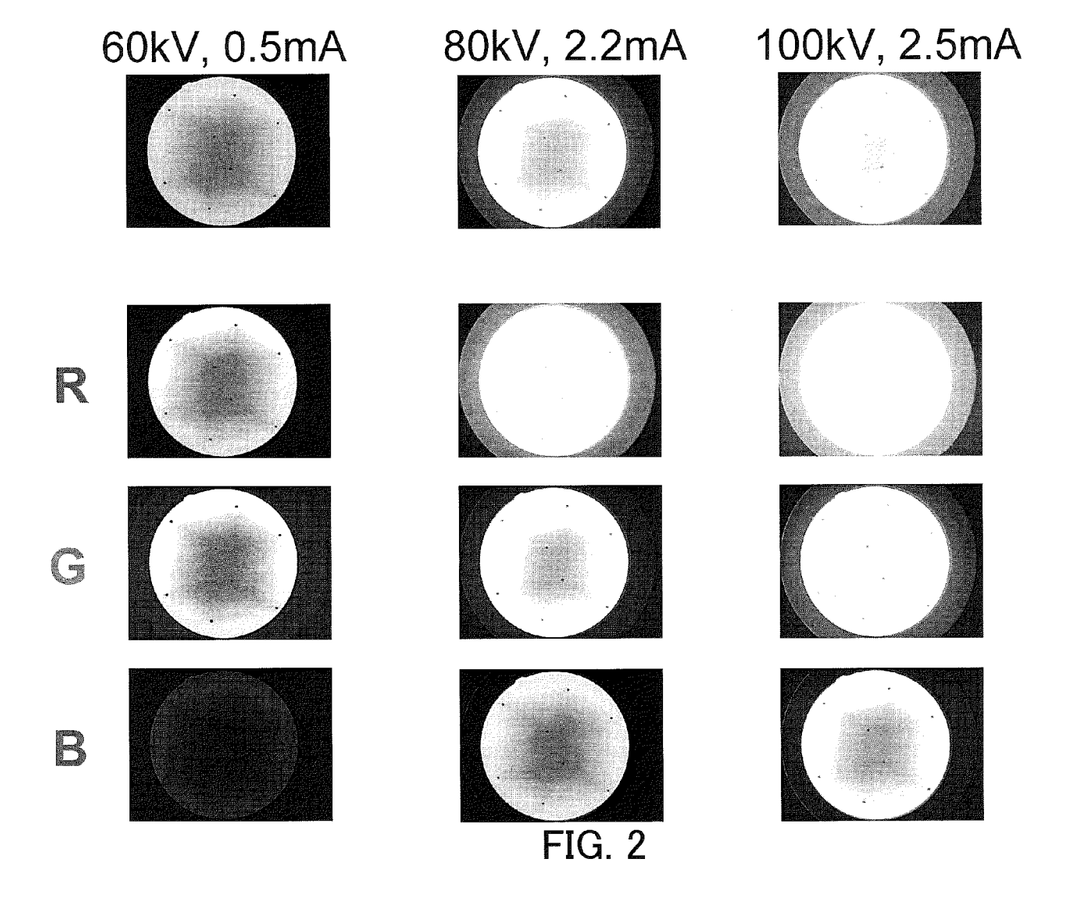
FIG. 2 is a diagram showing R, G, and B images having a plurality of X-ray intensities.

In the following, the image processing unit 34 will be described. As described above, in this embodiment, image signals having three different sensitivities, namely, R, G, and B signals, are obtained for a single-directional X-ray beam. FIG. 2 shows R, G, B images obtained when an X-ray is irradiated to a specimen, with three kinds of intensities. The specimen is a cubic plastic phantom with markers 14 placed at each of the eight corners thereof. It is observed that, among R, G, and B, images are different due to difference in sensitivities, and that ease in recognizing the marker 14 also differs. In this case, R is of the highest sensitivity, and B the lowest.

Figure 3:
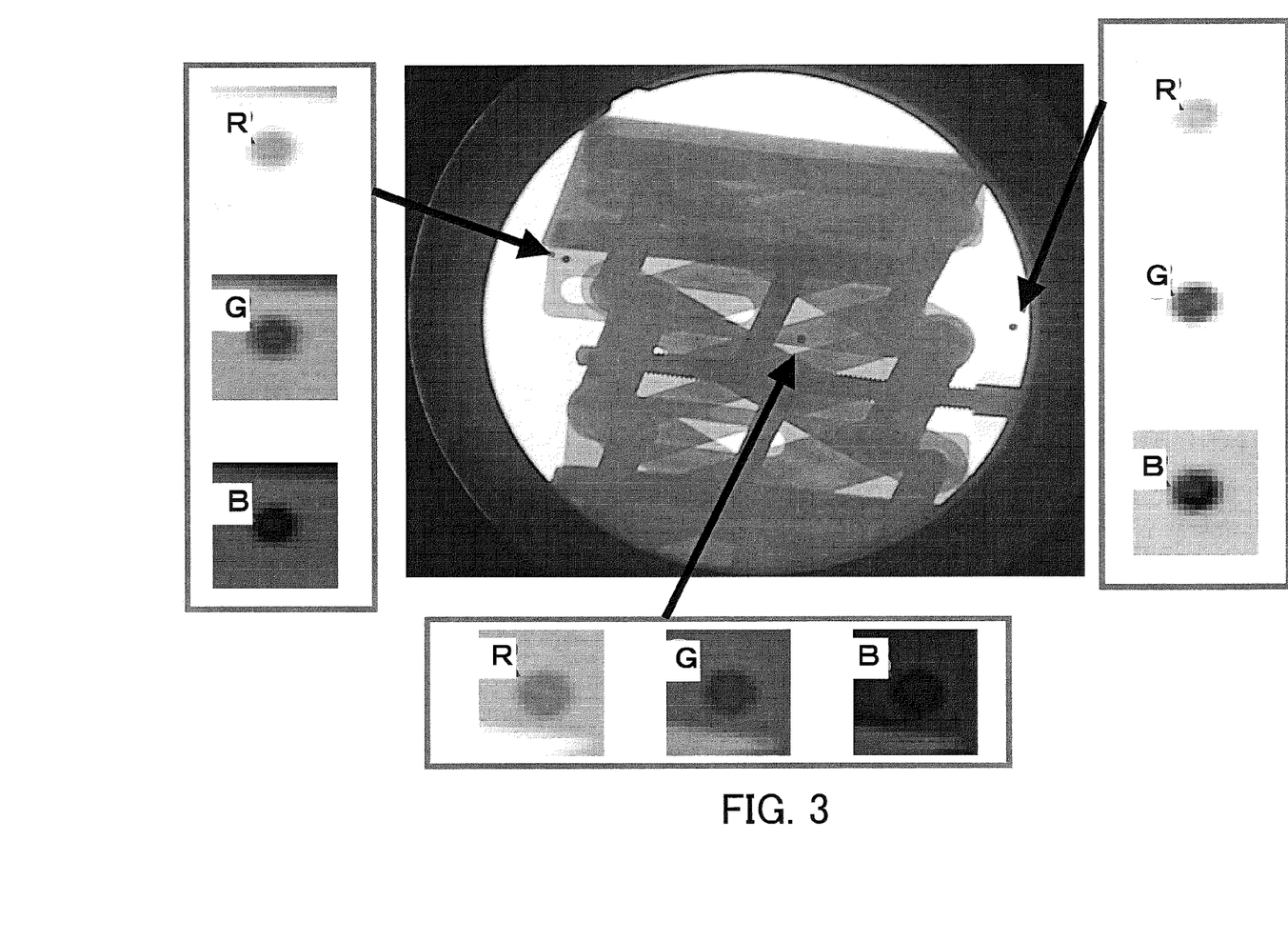
FIG. 3 is a diagram showing marker images at positions having different absorption rates.

FIG. 3 shows an image obtained when multiple markers 14 are placed in a phantom having material, similar to bone or the like, that readily absorbs X-rays, placed therein, specifically showing R, G, and B images of three respective markers 14. It is known that an image that clearly shows the marker 14 differs among the R, G, B images, depending on the position.

Direct Detection of Marker from Each Image

In this embodiment, the image processing unit 34 carries out pattern matching of a marker pattern independently for the respective R, G, and B images to detect the marker 14. Then, a marker 14 with the highest pattern matching score in the result obtained is employed, so that the coordinates of that marker 14 are determined as the position of the marker 14.

As described above, with use of a plurality of images simultaneously captured from different directions and having different sensitivities, it is possible to recognize, e.g., a marker 14 in a lung and a marker 14 hidden by high density material, such as bone, in any of the images having different sensitivities. Then, application of pattern matching independently for a plurality of images having different sensitivities enables accurate identification of the position of the marker 14 in different conditions.

Figure 4:
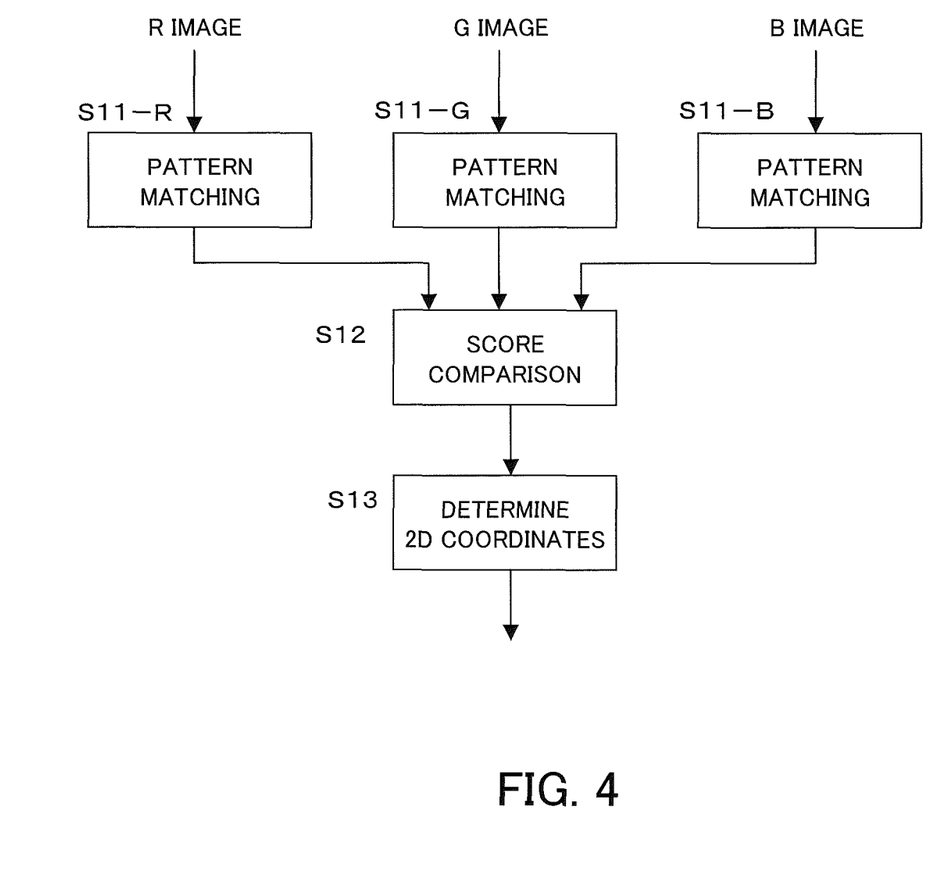
FIG. 4 is a flowchart of an example image process.

FIG. 4 shows a flowchart of a process carried out in the image processing unit 34. As described above, for the respective R, G, and B images, the pattern of the marker 14 is given pattern matching (S11-R, S11-G, S11-B). Specifically, the pattern matching is carried out through pattern matching between the image data on the marker 14 and the respective images supplied from the camera interface 32. In the above, a score relating to the degree of coincidence in pattern matching is stored for each of the markers 14 detected in the respective images. Note that each image may be subjected to edge detection before pattern matching. Further, in pattern matching, reference marker image data is defined for each color image. With the above, appropriate pattern matching can be achieved with respect to an image in each color. Further, a reference for use in a case with edge detection applied is preferably a marker image subjected to edge detection.

Thereafter, markers 14 at similar positions in the respective R, G, and B images are selected, and the scores thereof in pattern matching are compared with (S12). A marker 14 with the highest score is selected, and the 2D coordinates of the marker 14 in the image are determined (S13). In this manner, the coordinates of the marker 14 in an image are determined based on an image from one direction. This process is similarly carried out for the other direction. With the above, the coordinates of the marker 14 in images viewed from two directions are determined, and the data is supplied to the position determining unit 36.

For example, to track the marker 14 in a lung area, the position is calculated using an image of a low sensitive fluorescent body (e.g., B or G image), while to track the marker 14 hidden by a high density member, such as bone or the like, the position is calculated using a highly sensitive image (R image). This enables tracking of the marker 14, irrespective of a fluoroscopic condition.

Note that as the image intensifier 28 for obtaining images having different sensitivities, a color image intensifier apparatus (see Non-Patent Document 1) manufactured by Toshiba Power Systems Company and commercially available may be used.

As described above, as three images (R, G, B images) captured from the same direction and having different sensitivities can be simultaneously obtained in this embodiment, the accuracy in tracking the marker 14 can be improved even in a frequently changing condition by tracking using an image that enables most effective analysis. Further, appropriate adjustment of the X-ray image capturing sensitivity of three fluorescent bodies can widen the dynamic range. This enables tracking in a condition in which tracking is not conventionally possible. Further, in tracking multiple markers 14, it is possible to track the markers 14 even when fluoroscopic conditions differ greatly.

Marker Detection Through Operation Among Images

Figure 5:
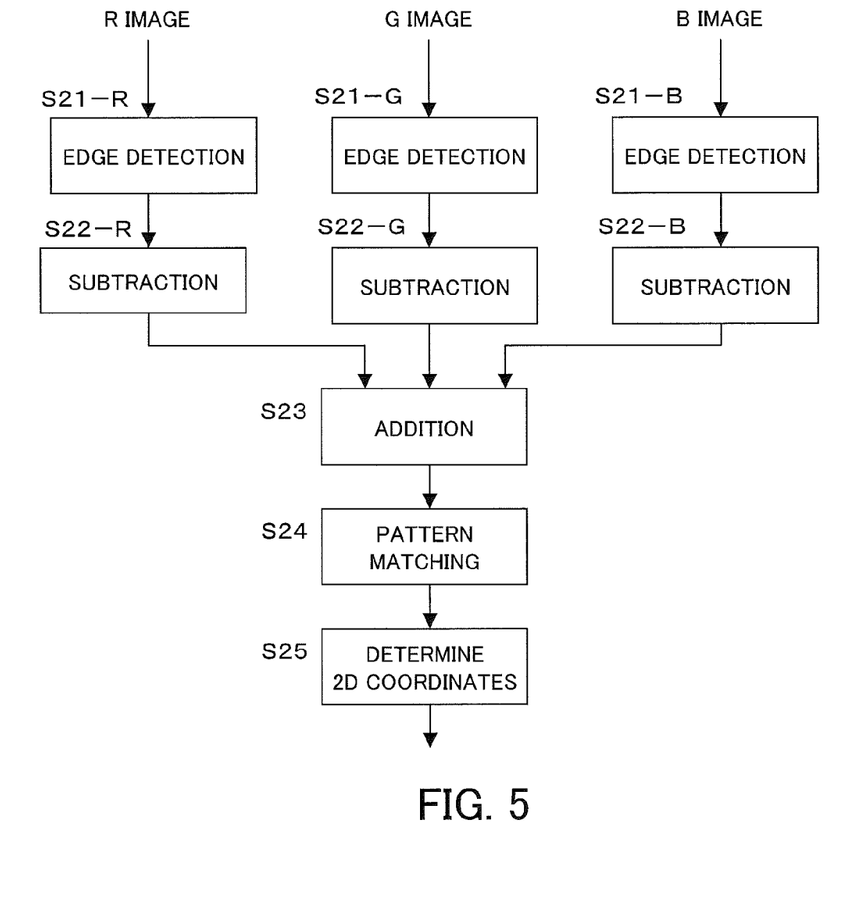
FIG. 5 is a flowchart of another embodiment of an image process.
Figure 6:
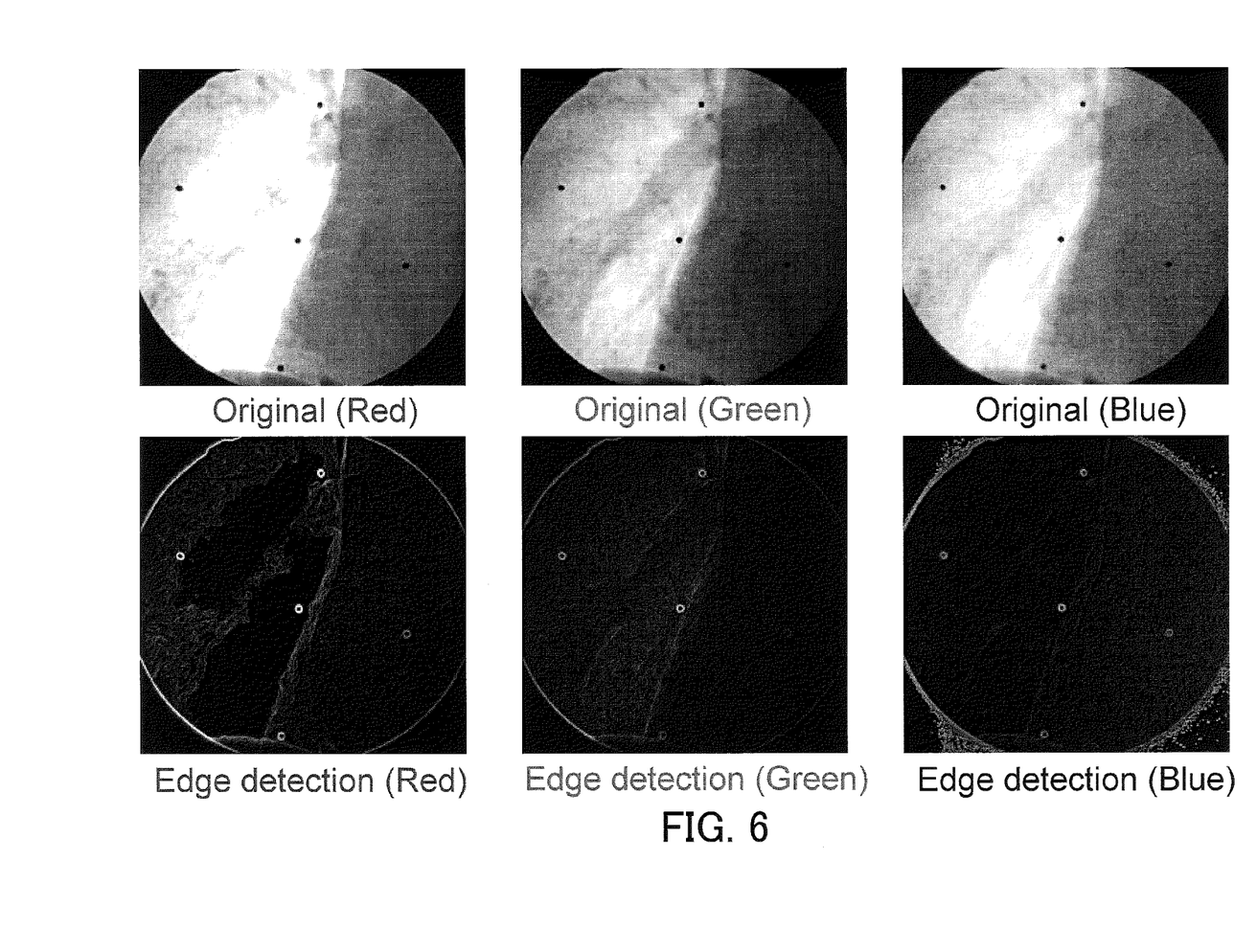
FIG. 6 is a diagram showing an original image and an image subjected to edge detection.

FIG. 5 shows another example of detection of the marker 14. In this example, edge detection (edge enhancement) is applied to the respective R, G, B images (S21-R, S21-G, S21-B). In edge detection, a part (edge) with a remarkable change in brightness is detected, utilizing a spatial differentiation value. With this edge process, an edge-enhanced image, such as is shown in the lower part of FIG. 6, is obtained from an original image in respective R, G, B colors, such as is shown in the upper part of FIG. 6. As the marker 14 has a higher X-ray absorption rate, compared to that of surrounding tissue thereof, the outer edge of the marker 14 is detected.

Thereafter, the original image is subtracted from the edge enhanced image (S22-R, S22-G, S22-B). Note that the original image for subtraction is used intact for each pixel data, and that pixel data of the original image is subtracted from pixel data of the edge enhanced image corresponding to each pixel. The pixel data is not minus data, and brightness of the pixel (the pixel data) is zero. With this subtraction, a subtraction image where change in brightness in a part other than the marker 14 is mostly deleted is obtained. Meanwhile, the brightness of the image of the marker 14 drops as well. Note that image data for subtraction may not necessarily be intact, and weighted subtraction, that is, weighted pixel data may be used for achieving a smaller range of change.

Thereafter, the obtained three subtraction images are subjected to an addition process (S23). With the above, a sum image where the contour of the marker 14 is more clearly defined can be obtained.

Figure 7:
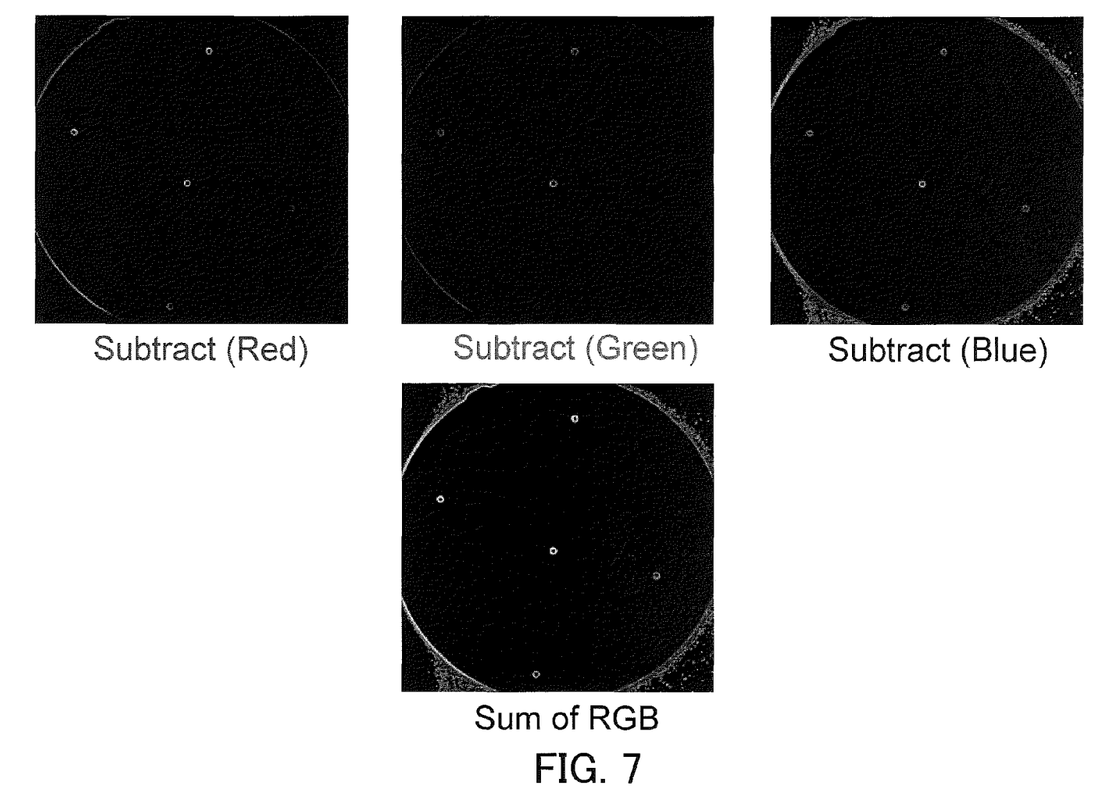
FIG. 7 is a diagram showing a subtract image and a sum image.

Then, for the thus obtained sum image, pattern matching is carried out (S24). In a sum image, an image where the contour of the marker 14 is clearly defined, such as is shown in the lower part of FIG. 7, is obtained. Therefore, accurate pattern matching can be carried out.

In particular, in the process in this embodiment, it is sufficient to apply pattern matching, which imposes a larger load in operation, to a single image. This enables a rapid operation and thus high-speed processing. That is, while edge detection, subtraction, and addition impose a remarkably smaller load in operation, compared to pattern matching, reduction in the number of applications of pattern matching to one enables reduction of a load in operation as a whole, which enables high speed processing.

Further, preferably, a reference image for use in pattern matching with a sum image is produced with edge detection, subtraction, and addition applied to a marker image in each color.

Preferably, the above described marker detection through operation among images in respective colors and the above described direct detection of a marker from each image are both carried out, so that a maker with the highest score is selected from among the detected markers.

"Others"

As described above, according to this embodiment, it is possible to effectively detect a target, such as the marker 14, or the like. Therefore, the embodiment can preferably be applied to use other than radiation therapy. For example, an X-ray fluoroscopic device is utilized in an airport or the like to detect a suspicious object. The detection aims to find a dangerous object, such as a metallic knife, in particular. In this view, the marker detection method according to this embodiment can be preferably used in detection of such a dangerous object.

Further, in image processing, γ correction and so forth is applied in order to obtain more natural display by adjusting the relative correlation between color data, such as an image or the like, and a signal in actually outputting the data. Such image processing can be desirably carried out when necessary.

In the above example, the marker 14 or a metallic dangerous object is referred to as a target. However, the target may be anything, such as a tumor, that has a different X-ray absorption rate from that of the background. For example, according to this embodiment, it is possible to obtain a clear image of a tumor.

Further, in radiation therapy, there is a demand for irradiating the minimum possible amount of therapy radiation to the spinal cord. According to the above described embodiment, it is possible to reliably track multiple markers. Therefore, preferably, while regarding a tumor and a backbone (vertebral column) as markers, the tumor is tracked on one hand, and the vertebral column is recognized on the other hand, so that the positional relationship between the tumor and the backbone is determined for controlling the irradiation. That is, when the determined 3D position of the tumor is within a predetermined range and the spinal cord is not within the predetermined range, therapy radiation is irradiated. With the above, it is possible to control irradiation of therapy radiation so that therapy radiation is irradiated to the tumor while irradiation toward the vertebral column is prohibited, so that irradiation of therapy radiation toward the spinal cord can be prevented. Note that in the above, although the organ desired to be avoided from being irradiated by therapy radiation is the spinal cord, the vertebral column is used as a marker which can be recognized through X-ray fluoroscopy is the vertebral column (backbone). As the positional relationship between the vertebral column and the spinal cord can be measured in advance, recognition of the position of the vertebral column through pattern matching enables calculation of the position of the spinal cord. Note that instead of recognition of a tumor and the vertebral column, a metallic marker can be used. Further, while regarding the vertebral column alone as a target, it is possible to determine the position of the vertebral column.

REFERENCE NUMERALS

10 therapy bed, 12 patient, 14 marker, 20 X-ray fluoroscopic device, 22 X-ray irradiating device, 24 X-ray tube, 26 collimator, 28 image intensifier, 30 camera, 32 camera interface, 34 image processing unit, 36 position determining unit, 38 control unit, 40 beam irradiation device.

The invention claimed is:

1. A method for tracking a moving target, comprising:
   repeating for each of a plurality of directions:
      obtaining a plurality of X-ray fluoroscopic images from a plurality of fluoroscopic devices, wherein each of the plurality of X-ray fluoroscopic images has different sensitivity for X-ray;
      performing pattern matching between an image of the target and each of the plurality of X-ray fluoroscopic images to identify a target image in each of the plurality of X-ray fluoroscopic images;
      identifying the target image with a highest pattern matching score;
      determining a two-dimensional position of the target based on a position of the target image with the highest pattern matching score;
   determining a three-dimensional position of the target based on the two-dimensional position of the target for each of the plurality of directions;
   repeating the determining a three-dimensional position of the target to thereby track the target.

2. The method according to claim 1, wherein the plurality X-ray fluoroscopic images are obtained in a plurality of fluorescent colors according to an intensity of fluoroscopic X-rays.

3. The method according to claim 1, wherein irradiation of a radiation therapy beam toward a living organ is controlled based on the three dimensional position of the target.

4. The method according to claim 3, wherein the irradiation of the radiation therapy beam toward the living organ is permitted or restricted only when the 3D position of the target is within a predetermined area.

5. A target tracking device for tracking a moving target comprising:
   a plurality of X-ray fluoroscopic devices configured to obtain a plurality of X-ray fluoroscopic images from each of a plurality of directions, wherein each of the plurality of X-ray fluoroscopic images in one direction of the plurality of directions has different sensitivity for X-ray;
   an image processing unit configured to, for each direction of the plurality of directions:
      perform pattern matching between an image of the target and each of the plurality of X-ray fluoroscopic images to identify a target image in each of the X-ray fluoroscopic images,
      identify the target image with a highest pattern matching score;
      determine a two-dimensional position of the target based on a position of the target image with the highest pattern matching score; and
   a position determining unit configured to determine a 3D position of the target, based on the two-dimensional position of the target for each of the plurality of directions,
   wherein the 3D position of the target is repeatedly determined to thereby track the target.

6. The target tracking device according to claim 5, wherein the plurality of X-ray fluoroscopic devices obtains X-ray fluoroscopic images in a plurality of fluorescent colors according to an intensity of fluoroscopic X-rays.

7. A radiation therapy apparatus including the target tracking device according to claim 5, wherein irradiation of a radiation therapy beam toward a living organ is controlled based on the 3D position of the target.

8. The radiation therapy apparatus according to claim 7, wherein the irradiation of the radiation therapy beam toward the living organ is permitted or restricted only when the 3D position of the target is within a predetermined area.

* * * * *